United States Patent [19]

Ledent

[11] Patent Number: 5,606,106

[45] Date of Patent: Feb. 25, 1997

[54] HEXAMETHLENE PHOSPHONATE CONCENTRATE

[75] Inventor: Michel A. O. Ledent, Saint-Marc, Belgium

[73] Assignee: Monsanto Europe S.A., Brussels, Belgium

[21] Appl. No.: 508,501

[22] Filed: Jul. 28, 1995

[30] Foreign Application Priority Data

Sep. 1, 1994 [EP] European Pat. Off. .............. 94870145

[51] Int. Cl.$^6$ ...................................................... C07F 9/38
[52] U.S. Cl. ............................................... 562/14; 562/16
[58] Field of Search ........................................ 562/14, 16

[56] References Cited

U.S. PATENT DOCUMENTS

| | | | |
|---|---|---|---|
| 3,816,333 | 6/1974 | King et al. | 252/389 A |
| 4,477,390 | 10/1984 | Ledent et al. | 260/502.5 E |
| 4,548,757 | 10/1985 | Wevers et al. | 260/502.5 E |
| 4,615,840 | 10/1986 | Ledent et al. | 260/502.5 E |
| 4,728,460 | 3/1988 | Ledent et al. | 260/502.5 E |

FOREIGN PATENT DOCUMENTS

| | | |
|---|---|---|
| 047150 | 3/1982 | European Pat. Off. . |
| 0125766 | 11/1984 | European Pat. Off. . |

*Primary Examiner*—Gary Geist
*Assistant Examiner*—Barbara S. Frazier
*Attorney, Agent, or Firm*—Fitzpatrick, Cella, Harper & Scinto

[57] ABSTRACT

Concentrated aqueous hexamethylene phonic acid solutions are described containing, in addition to high levels e.g. 40%–50% of phosphonic acid a narrowly defined level of non-oxidizing mineral acid, preferably hydrochloric acid.

4 Claims, No Drawings

HEXAMETHLENE PHOSPHONATE CONCENTRATE

This invention related to storage stable aqueous methylene phosphonate acid concentrates containing at least 20% by weight of phosphonic acid and from, at least 18% to 22% by weight of a non-oxidizing acid, particularly hydrochloric acid. The methylene phosphonic acid has the formula

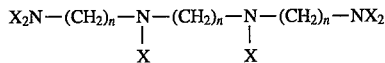

wherein X is —CH$_2$PO$_3$H$_2$, —CH$_3$, —H and mixtures thereof with the proviso that at least one X is —CH$_2$PO$_3$H$_2$ and n is an integer of 1 through 5.

The phosphonic acid preferably represents from about 30% to about 55% by weight.

Aqueous solutions of sodium salts of the methylene phosphonic acid component in accordance with this invention are commercially available under the tradename DEQUEST ®2086. The methylene phosphonates corresponding to the foregoing general formula frequently contain a mixture of D6A {hexamethylene phosphonic acid derivative} and D4A {tetramethylene phosphonic acid derivative}. The D6A component is the major component and generally represents at least 40%, such as from 55% to 85%, usually from 70% to 85%, based on the combined weight of D6A and D4A. The weight ratio of the D6A to the D4A phosphonic acid is frequently in the range of from 2:6 to 19:1, more preferably from 2:15 to 16:1. Other phosphonic acids such as hydroxymethyl phosphonic acid may be present in additive levels below 10%. In addition, the phosphonate solution can also contain small amounts of phosphorous acid and phosphoric acid and also hydrochloric acid at low level, usually not more than 12%, by weight of the solution. Typical commercial products can, in addition to NaOH, also be neutralized with KOH, NH4OH and amines to a pH "as is" of at least 4.0–4.5 to thus improve storage stability also in the presence of low percentage of chloride. An "as is" pH of below 4.0 leads to substantial stability problems and generally yields complete solidification on storage.

Conventionally, aqueous phosphonate solutions are described in terms of their concentration of "total active acid" which is measured by titrating the phosphonic groups with NaOH and convening the results to the stoichiometrically equivalent concentration of D6A. The concentration of methylene phosphonic acid, expressed as active acid, is normally from about 94% to 98% of the actual concentration of the methylenephosphosphonic acid.

It was known that the solubility of aminomethylenephosphonic acid can be, to a certain extent, increased by HCl in the solution. Alternatively, some phosphonic acids such as aminotri (methylene phosphonic acid) behave differently and their solubility in aqueous solutions at ambiant temperature is known to be adversely affected by increasing the amount of hydrochloric acid beyond a certain, fairly low, level. It is also well known that the tetraphosphonates of ethylenediamine and hexamethylenediamine are substantially water-insoluble and their solubility is adversely affected by the addition of non-oxidizing mineral acids.

The majority of aminomethylene phosphonic acid solutions are, upon storage under ambiant conditions, known to be subject to considerable stability problems. Precipitation occurs and additional handling operations, such as heating and stirring are usually required. The problem is well known and the prior an is possessed of a variety of remedies which could not be expected to be beneficial in relation to the hexamethylene phosphonate concentrates herein.

EP-A-0.0147.150 teaches that concentrated solutions containing about 30–55% of diethylenetriaminepentamethylene phosphonic acid can be rendered storage stable through the addition from 12% to 17% of a non-oxidizing acid such as hydrochloric acid. GB-A-2.138.424 discloses a fairly broad range of partially neutralized aminomethylene polyphosphonates solutions having improved long term stability. It was also generally known that, except for the aminopentamethylene polyphosphonate species in accordance with EP-A-0.047.150, acid stabilization was not often a useful approach for solving the problem.

The applicant has now, in part, discovered that aqueous storage-stable concentrates can be prepared containing at least 20% by weight of narrowly defined aminomethylene phosphonic acid and from, at least 18% to 22% by weight of a non-oxidizing acid.

As used herein, the term "non-oxiding acid" means a mineral acid which, at a concentration of 20% by weight, does not significantly, i.e. more than 10%, oxidize D6A and/or D4A in aqueous concentrates containing 20% by weight of D6A and/or D4A. Unless expressed differently, percentage indications stand for percent by weight.

The invention herein relates to aqueous storage-stable concentrates containing high levels, at least 20%, of an aminomethylene phosphonic acid having the formula wherein

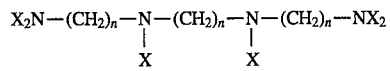

wherein X is —CH$_2$PO$_3$H$_2$, —CH$_3$, —H and mixtures thereof with the provisio that at least one X is —CH$_2$PO$_3$H$_2$ and n is an integer of 1 through 5.

A most preferred species is D6A, which is trialkylenetetraminohexamethylene phosphonic acid. In preferred executions, the D6A component frequently represents from 75% to 85% based on the weight of total phosphonic acid. D4A, which is trialkylenetetraamino-tetramethylene phosphonic acid is usually formed, together with D6A, in an amount of from 5% to 10%, based on the weight of total phosphonic acid. Minimal quantities, usually below 5%, of other phosphonic acids, phosphorous and/or phosphoric acids can also be present. In D4A, hydrogen attached to the nitrogen can be substituted by a CH$_3$ moiety.

The alkylene moiety is represented by methylene groups having an n in the range of from 1 through 5, preferably 2 and/or 3.

The concentrate frequently contains from 35% to 60%, preferably from 40% to 50% of the methylene phosphonic acid (expressed as D6A).

The most preferred non-oxidizing mineral acid is hydrochloric acid. Other non-oxidizing acids inclusive of sulfuric, phosphoric, phosphorous or hydrobromic acid and mixtures of such suitable non-oxidizing acids can also be used.

The acid can be added to the phosphonate by any convenient procedure to thus yield the claimed concentrate. The acid level is expressed in reference to the total acid in the concentrate. The finished phosphonate reaction mixture usually contains a certain level of non-oxidizing mineral acid. The acid level in the concentrate shall be adjusted accordingly.

The concentration of the non-oxidizing mineral acid is very critical and shall be at least 18% to 22%, preferably at least 18% to 20%. Expressed differently, the concentrate containing from 40% to 55% of the essential phosphonate shall contain at least 0.495 up to 0.61 g equivalent acid/100 g of concentrate.

In addition to the essential phosphonate component and the non-oxidizing mineral acid, the claimed concentrates can contain additive levels of various other ingredients selected for the purpose of producing and delivering, in the context of the concentrate, their art-established activity. Examples of the like additives can include sequestrants and chelants other than the essential phosphonates, perfumes, colorants, dyes, opacifiers and so on.

The invention herein is illustrated by means of experimental showings.

Solutions 1 through 8 containing various concentrations of D6A and D4A in a weight ratio of 92:8 and hydrochloric acid are prepared in a conventional manner thereby using a concentrated (~33%) hydrochloric acid solution. The concentrate is mixed and seeded with pure D6A crystals and stored at 20° C. A concentrate qualifies as a stable concentrate in accordance with this invention if the seeds dissolve at 20° C. to yield a clear concentrate which remains free of solids at 20° C. for a period of at least 24 hours after seeding.

The experimental showings are summarized as follows:

EXAMPLES 1–8

| SOLUTION No. | % ACTIVE ACID | % HCl | Grms Equi/ 100 grm solution | OBSERVATIONS |
|---|---|---|---|---|
| 1 | 50 | 13.1 | 0.36 | Completely solidified |
| 2 | 50 | 15.1 | 0.41 | Undissolved seeds with further precipitation |
| 3 | 45 | 16.8 | 0.46 | Seeds undissolved |
| 4 | 40 | 18.5 | 0.51 | Stable |
| 5 | 40 | 15.4 | 0.42 | Undissolved seeds with further precipitation |
| 6 | 40 | 17.2 | 0.47 | Seeds undissolved |
| 7 | 40 | 13.1 | 0.36 | Completely solidified |
| 8 | 35 | 20.3 | 0.56 | Stable |

These examples show that, against expectations, a narrowly defined level of non-oxidizing mineral acid produces desirable and meaningful concentrate stability benefits.

I claim:

1. Aqueous storage-stable concentrate comprising at least 20% by weight of an aminomethylene phosphonic acid having the formula

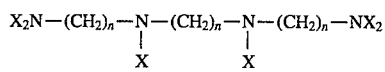

wherein X is —$CH_2PO_3H_2$, $CH_3$, H and mixtures thereof with the proviso that at least one X is —$CH_2PO_3H_2$, n is an integer of 1 through 5 and from at least 18% to 22% by weight of a non-oxidizing mineral acid.

2. The aqueous concentrate according to claim 1 wherein the methylene phosphonic acid is a mixture of trialkylenetetraaminohexamethylene phosphonic acid (D6A) and trialkylenetetraaminotetramethylene phosphonic acid in a weight ratio, of hexa to tetra species of from 2:6 to 19:1.

3. The aqueous concentrate according to claim 2 wherein the methylene phosphonic acid represents from 35% to 60% by weight.

4. The aqueous concentrate according to claim 2 wherein the non-oxidizing mineral acid is hydrochloric acid which is present in an amount of at least 18% to 20% by weight.

* * * * *

UNITED STATES PATENT AND TRADEMARK OFFICE
CERTIFICATE OF CORRECTION

PATENT NO. : 5,606,106
DATED : February 25, 1997
INVENTOR(S) : Michel A. O.Ledent et al.

It is certified that error appears in the above-identified patent and that said Letters Patent are hereby corrected as shown below:

Abstract, first line, "phonic" should read --phosphonic--.
Abstract, fourth line, "preferrably" should read --preferably--.
Column 1, line 50, "Methylenphosphophonic" should read --Methylenephosphonic--.
Column 2, line 3, "EP-A-0.0147.150" should read --EP-A-0.047.150--.
The Title and column 1, line 1, "Hexamethlene" should read --Hexamethylene--.
Column 1, line 46, "convening" should read --converting--.
Column 1, line 67, "prior an" should read --prior art--.

Signed and Sealed this

Seventeenth Day of April, 2001

Attest:

NICHOLAS P. GODICI

Attesting Officer

Acting Director of the United States Patent and Trademark Office